United States Patent [19]

Acord

[11] 4,000,974
[45] Jan. 4, 1977

[54] SAMPLE RESIDUE CLEANING SYSTEM FOR BIOLOGICAL ANALYZERS

[75] Inventor: William A. Acord, Claremont, Calif.

[73] Assignee: Beckman Instruments, Inc., Fullerton, Calif.

[22] Filed: Mar. 31, 1976

[21] Appl. No.: 672,081

Related U.S. Application Data

[62] Division of Ser. No. 504,390, Sept. 9, 1974.

[52] U.S. Cl. .......................... 23/230 R; 23/253 R; 141/130
[51] Int. Cl.² ................... B65B 43/56; B67C 3/16; G01N 33/16; G01N 1/14
[58] Field of Search ............ 23/230 R, 253 R, 259; 73/423 A, 423 R; 141/130, 284

[56] References Cited

UNITED STATES PATENTS

| | | | |
|---|---|---|---|
| 2,879,141 | 3/1959 | Skeggs | 23/253 R |
| 3,197,285 | 7/1965 | Rosen | 23/259 X |
| 3,266,322 | 8/1966 | Negersmith et al. | 23/253 R |
| 3,427,135 | 2/1969 | Delavin et al. | 23/253 R |
| 3,617,222 | 11/1971 | Matte | 23/253 R X |
| 3,701,716 | 10/1972 | Deuringer et al. | 23/259 X |
| 3,853,008 | 12/1974 | Hoffa et al. | 23/253 R X |

Primary Examiner—Robert M. Reese
Attorney, Agent, or Firm—R. J. Steinmeyer; R. R. Meads

[57] ABSTRACT

Method and apparatus for picking up liquid sample material, such as blood serum, in a sample pick-up probe and for ejecting the sample from the probe into a reagent chemically reactive with the sample for analysis. Before ejecting the sample from the probe, the probe is inserted into the reagent for a period of time sufficient for the reagent to consume any residue of sample adherent to the exterior of the probe. Thereafter, the sample to be analyzed is ejected from the probe into the reagent and the resulting sample-reagent reaction is measured. Isolation between the sample within the probe and the reagent may be maintained while the probe is in the reagent by a bubble of air drawn into a tip end of the probe before inserting the probe into the reagent. Since the sample residue adherent to the probe is removed before ejecting the sample material for analysis, the residue is eliminated as a source of analysis error and, in addition, is eliminated as a source of carryover contamination of the next sample to be picked up by the probe.

7 Claims, 11 Drawing Figures

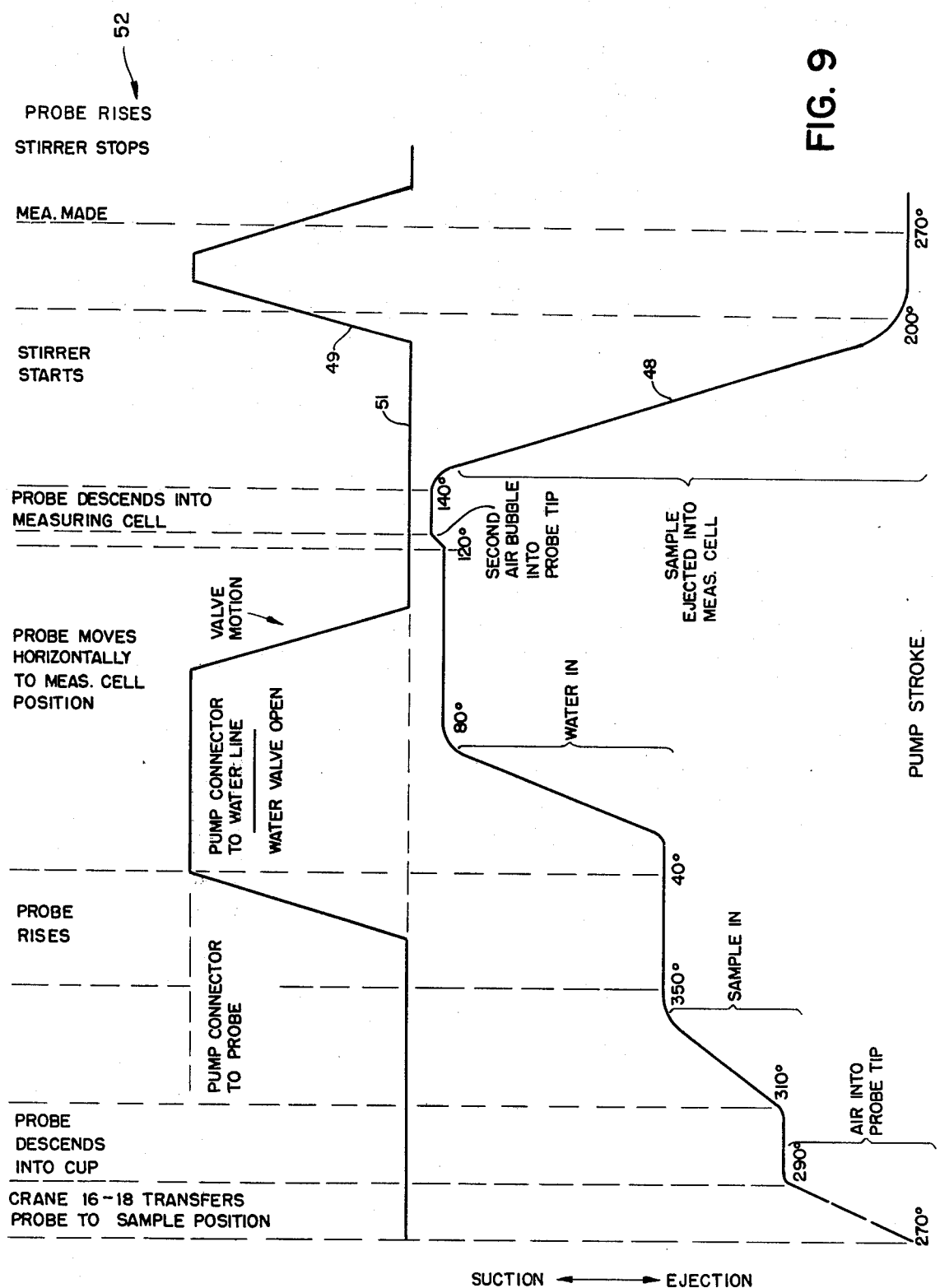

SAMPLE RESIDUE CLEANING SYSTEM FOR BIOLOGICAL ANALYZERS

This is a division of application Ser. No. 504,390, filed Sept. 9, 1974 and entitled "Sample Residue Cleaning System for Biological Analyzers.

The probe is then inserted into the sample cup 13, and pump 35 is again actuated to draw a sample slug 43 into the probe.

BACKGROUND OF THE INVENTION

A. Field of the Invention

The invention is concerned with the analysis of samples withdrawn from a sample cup by a probe and thereafter injected into a measuring cell containing a suitable reagent with some reaction between the sample and the reagent being measured to accomplish the analysis. The invention has its application particularly to medical procedures where samples of body fluids, blood plasma or serum and the like can be analyzed promptly after the sample is withdrawn from the patient. In such procedures the analysis is determined by obtaining the glucose value or the BUN (Blood-urea-Nitrogen) value when the sample is ejected into an enzyme reagent and the maximum rate of reaction is measured. In one procedure glucose is determined by means of oxygen rate method employing an oxygen sensor, in another procedure conductivity rate method is employed. Owing to the fact that the analysis is determined by the maximum rate of the reaction which is permitted to go on for a period of time, and this rate is critically determined by the quantity of sample reacting, it is very important that precisely metered samples be introduced into the measuring and reacting cells and that no extraneous material be permitted to enter the cell.

B. Description of the Prior Art

A glucose analyzer is described in an operating manual published by Beckman Instruments, Inc. of Fullerton, California, identified as Beckman Instructions 015-83513-F November, 1973, 731198 015-083513, copyright 1969. This manual describes how a precise volume of sample is manually pipetted into enzyme reagent in a cell containing a sensor that responds to oxygen concentration. Solid state electronic circuitry determines the rate of oxygen consumption, which is directly proportional to the concentration of glucose in the sample. In the description of pipetting methods it is pointed out that operator performance during sample introduction determines the quality of results that the instrument will furnish and that close attention to the details of the sampling procedure is required if the precision of the instrument is not to be compromised. It is also explained that, for pipettes of the type having a significant "dead volume" remaining air volume within the enclosed sealed portion of the sampling system, the amount of sample picked up is dependent upon the depth to which the tip is immersed into the liquid. In this type of pipette a volume of air is displaced and the sample picked up by the movement of a sealed piston. The operating manual also explains that the liquid level effect does not occur when a special type of pipette is employed with three positions of the actuator instead of only two.

Nevertheless there is also the necessity for avoiding retention of a residue of sample on the outside of the pipette tip, since the sample material retained on the outside of the pipette tip can represent a significant fraction of 10 $\mu$l, which is the order of magnitude of the samples. Wiping off the tip with tissue must be avoided because there is a risk of incomplete wipe-off or of withdrawing liquid from the pipette by capillary action and also the possibility of infection of the operator in the case of certain fluids being analyzed. A less operator-sensitive technique is therefore recommended which consists of dipping the tip into a distilled water rinse. As the tip is slowly withdrawn from the rinse water, surface forces strip liquid from the outside of the tip and eliminate the need for wiping with a tissue.

The said operating manual also describes a measurement cell with separate, manually operated syringe-type plunger pumps for filling the measurement cell from a reagent reservoir and for draining the measurement cell after an analysis has been made by means of the oxygen sensor.

Liquid analysis apparatus having an oxygen sensor, a magnetically coupled stirrer in a measurement cell, two thumb operated barrel pumps with spring return, one for filling the measurement cell with reagent and the other for draining reagent from the measurement cell is described in U.S. Pat. No. 3,701,716 issued to Deuringer, Ray and Sternberg.

Apparatus for dipping a pair of sample probes into a sample cup, and transferring them to horizontally separated positions for ejection of the samples into two measurement cells is described in U.S. Pat. No. 3,853,008. of Jack L. Hoffa assigned to the same assignee as the present application. Another form of apparatus for automatically aspirating sample form sample cups and transferring samples to reagent cells is described in U.S. Pat. No. 3,617,222 to Matte. The latter patent also describes mechanism for bringing successive sample cups or test tubes into position.

U.S. Pat. No. 3,266,322 Negersmith et al. describes liquid sample supply and wash apparatus for an automatic analysis system with different sample cups on a rotating plate. A rotating plate cup carrier is described also in U.S. Pat. No. 2,879,141 to Skeggs.

It is an object of the invention to provide an improved procedure for clinical sample analysis in which a sample is not merely picked up and introduced into a reaction cell with great precision but also without contaminating carryover into the next sample. A further object of the invention is to provide fully automatic or semi-automatic apparatus for sample analysis, especially for glucose analysis and for blood urea nitrogen analysis in which sample contamination is avoided.

It is still another object of the invention to provide an improved system for cleaning probe tips and removing external sample residue coating.

Other and further objects, features and advantages of the invention will become apparent as the description proceeds.

SUMMARY OF THE INVENTION

In carrying out the invention in accordance with an improved form thereof, sample cups are provided, each containing a different sample such as blood serum to be analyzed. A sample probe, or a pair of probes connected to sample pumps and each having a sample tip, is provided. Each probe is adapted to be inserted below a liquid level in the sample cup. The sample pump is arranged for withdrawing sample from the cup through the tip into the probe. A crane is provided for lifting the probes and transferring each of the probes, to a horizontally separated measuring cell which is open at the top so that the sample probes may be lowered into separate measuring cells with each tip under the surface of liquid reagent contained in the measuring cell. Reagent supply reservoirs are provided and each measuring cell is provided with a reagent input port and a drain port connected to pump means for supplying suitable reagent to the measuring cell and later draining. There may be a separate reagent fill pump connected to the input port and a drain/wash pump connected to the reagent output port. Preferably there is a stirring motor carrying a rotatable magnet magnetically coupled to a stirrer, rotatably mounted within each measuring cell.

Suitable means are provided for obtaining an analysis after a sample has been injected into the measuring cell by the sample pump connected to the sample pick-up probe. The analysis means may take the form of a measurement sensor such as an oxygen sensor or a conductivity sensor connected to suitable solid state circuitry having a digital readout. Preferably a quantity of distilled water is also injected into the measuring cell following the sample to make sure that all of the sample is ejected into the reacting and measuring cell. The exact volume of water is not critical since the water does not affect the rate of reaction. It is preferably, however, comparable with the volume of the sample. Nevertheless, it is important to prevent diffusion of the sample into the water column from which the water is derived. Consequently, the water used with each sample in a probe is separated from the sample in that probe by an air bubble. In addition an air bubble is also drawn into the tip of the probe after a sample has been drawn in order to prevent diffusion of reagent into the tip and premature commencement of reaction between the reagent and the sample in the probe.

A unique feature of the apparatus is provision, in a programming apparatus for controlling the analyzer, of means for delaying ejection of sample into the reagent, holding the probe in the reagent, and deactivating the measurement sensor during the delay period with the probe tip immersed in the reagent, preferably while the stirrer is operating to wash the outside of the probe, in order to consume any residue on the outside of the probe during the delay period, so that the reaction is precisely limited to the metered quantity of sample inside the probe and also in order that a clean sample may be obtained when the pick-up probe is again immersed in a sample cup.

In the type of analysis involved, the quantity of glucose, BUN, or whatever may be a constituent of the sample for which the analysis is made, is determined by the maximum rate of a reaction which takes place between the sample and a reagent. In the case of body fluids the reagent is an enzyme. It is oxydase for the glucose analysis and urase for the BUN analysis, e.g. the reaction continues for a period of time until the sample is entirely consumed by the reagent. An excess of reagent is provided in the measurement cell, so that the volume of reagent does not affect the result. However, in the preferred procedure the analysis is not concerned with the total quantity of reaction products, or even the rate of reaction at any given time or the average rate, but with the maximum rate of the reaction. This value depends critically upon the quantity of sample introduced into the reagent.

Consequently, it is necessary that only the metered quantity of sample be permitted to enter the reagent and that no residue be present on the outside of the probe tip when the rate is being measured.

After the delayed immersion has continued long enough to assure cleaning of the outside of the sample probe, the sample is ejected from the probe into the reagent in the measuring cell, the stirrer remains energized and the measurement sensor is activated to obtain an analysis. Thereafter, as in conventional apparatus, the drain port is opened, the drain and wash pump is actuated and the mixture of reagent and sample is drained from the measuring cell preparatory to receiving fresh reagent, cleaning a subsequently immersed pick-up probe and making a subsequent analysis.

Another important feature of the invention is thus providing the air bubbles in the tip of the probe and in the probe between the sample and the water in the probe.

A better understanding of the invention will be afforded by the following detailed description considered in conjunction with the accompanying drawings. Those features of the invention which are believed to be novel and patentable are pointed out in the claims appended hereto.

DRAWINGS

Figure 4:
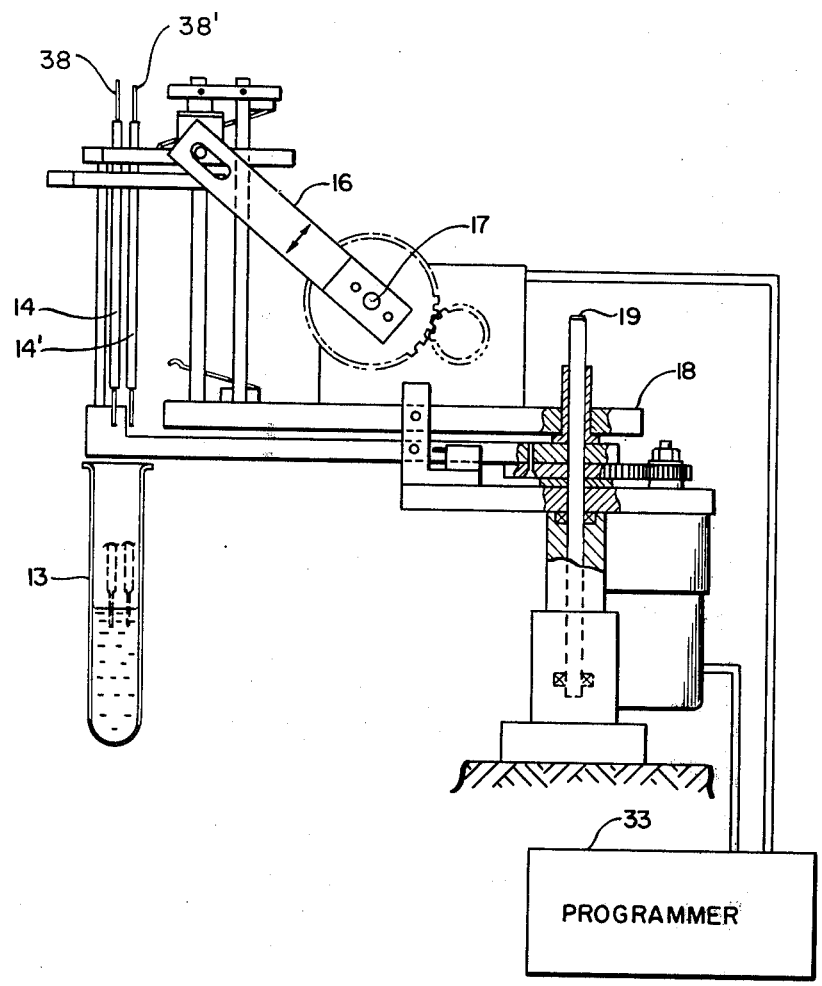

FIG. 4 is a diagram representing schematically, in elevation, certain structural elements of an automatic analyzer for two simultaneous analyses with crane mechanism for lowering and lifting a pair of sample probes successiveluy into a series of sample cups and for transferring the probes from each of the sample cups to a pair of measuring and reaction cells containing reagent and connected to a programmer having internal circuitry (not shown) for controlling the sample pump, reagent pump means, stirrer control mechanism and measurement sensor control mechanism as well as controlling the mechanism for lowering, lifting and transferring the sample probe and for bringing successive sample cups into position for enabling the probe to pick up sample.

Figure 5:
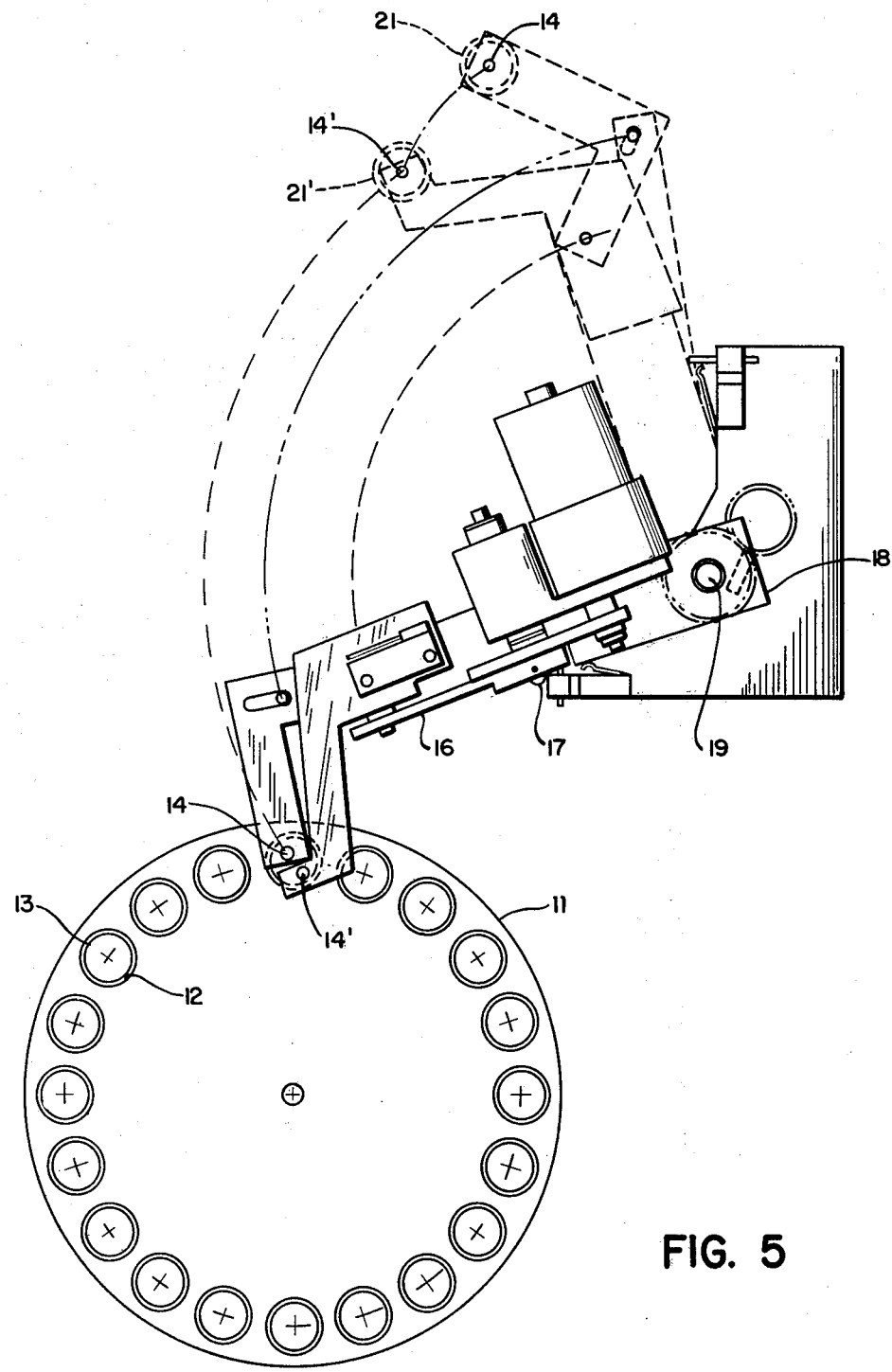
Figure 6A:
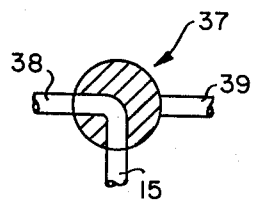
Figure 6:
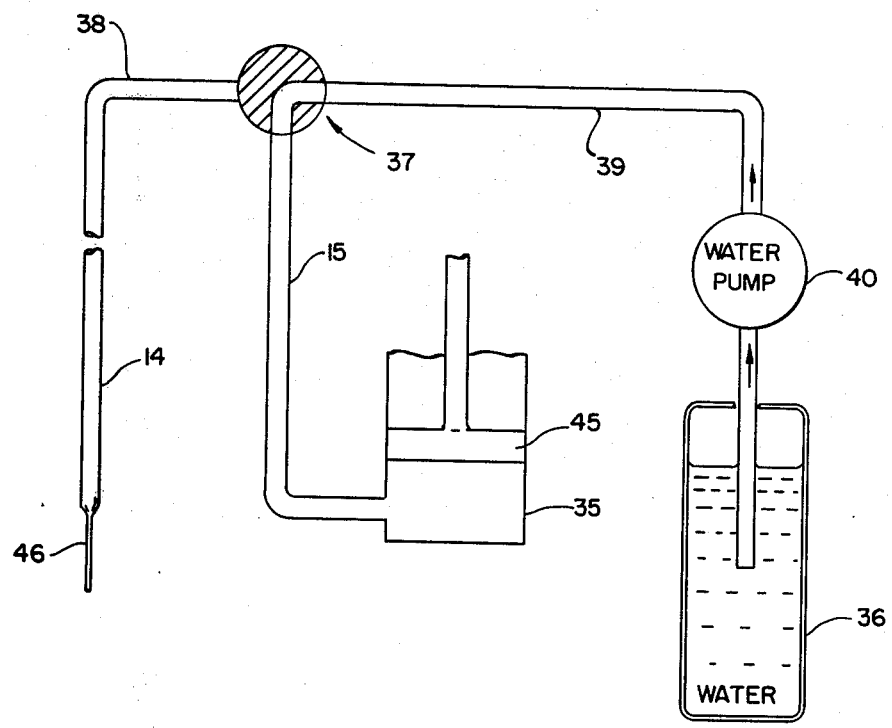
Figures 7, 8:
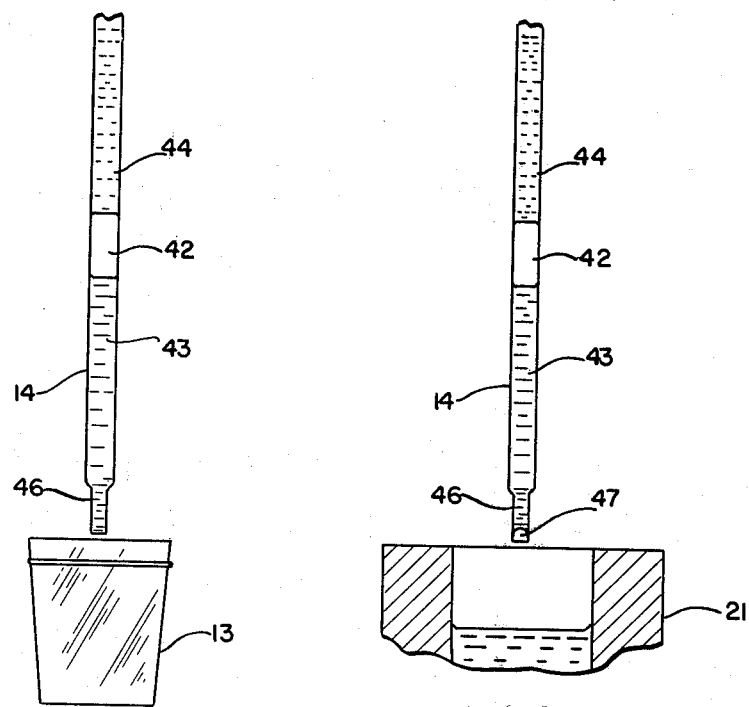
Figure 10:
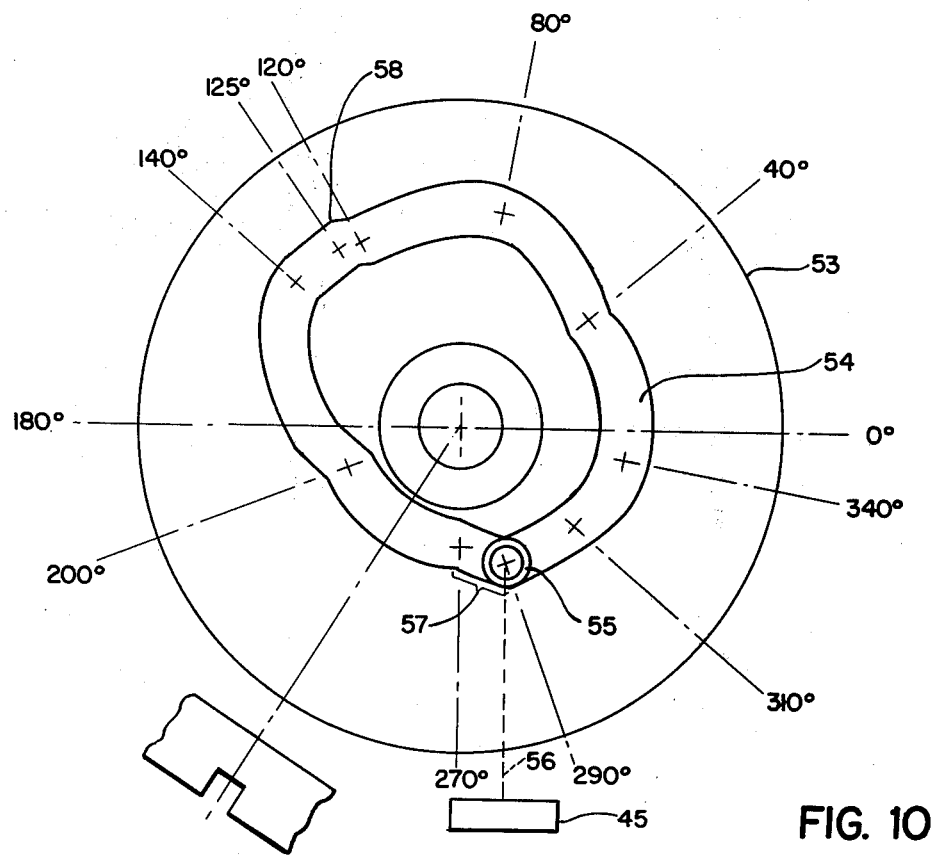

FIG. 5 is a plan view of the apparatus of FIG. 4;

FIG. 6 is a schematic diagram of tubing and valve connections for the probe and sample pump employed in the apparatus represented in FIGS. 1–5, showing a changeover valve in the position for connecting the sample pump line to a water line;

FIG. 6a is a fragmentary diagram of the changeover valve portion of FIG. 6 showing the valve in the position for connecting the pump line to the probe;

FIG. 7 is a fragmentary schematic diagram showing the probe in the position over the measuring cell before lowering for an analysis and showing the location of water and air slugs or bubbles in the probe, with one air bubble separating the water and the sample, and the other air bubble in the probe tip;

FIG. 8 is a fragmentary view corresponding to FIG. 7 but showing the probe over the sample cup with the air slug separating the sample from the water slug after the sample and water have been taken in but before the probe has been transferred to a position above the measuring cell and an air bubble has been drawn into the probe tip;

FIG. 9 is a set of graphs illustrating the stroke of the sample pump, the valve motion and the timing of various events in relation to the sample pump stroke; and FIG. 10 is a fragmentary diagram of a portion of the apparatus showing a cam arrangement for accomplishing the pump stroke illustrated in FIG. 9.

Like reference characters are utilized throughout the drawing to designate like parts.

DETAILED DESCRIPTION OF THE INVENTION

As illustrated in FIG. 5, there is a rotating plate 11 having suitable cavities 12 at the periphery, circumferentially spaced to receive test tubes or sample cups 13. A pick-up probe 14 is provided having generally vertical lifting and lowering motion. The pick-up probe 14 is connected through flexible tubing 38 and 15 (FIG. 6) to a sample pump 35. For dual analysis there is a second pick-up probe 14 with similar tubing 38' (FIG. 4) and 15' (not shown).

For imparting lifting and lowering motion to the pick-up probes 14 and 14', they are mounted in a suitable manner upon an arm 16 which is vertically movable, being for example pivoted about a horizontal axis 17. As represented schematically in FIG. 5, the arm 16 also has a horizontal motion, its pivot axis 17 for example being mounted upon a turntable or an arm 18 which has a vertical pivot axis 19.

Figure 3:
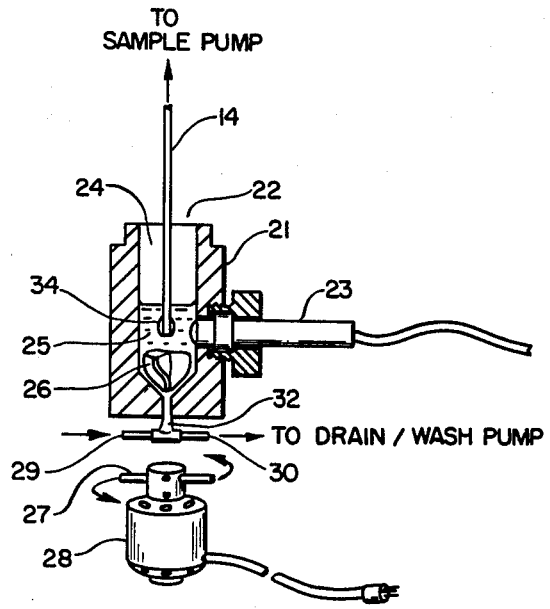
FIG. 3 is a schematic diagram partially in section of a measuring cell containing reagent showing the sample pick-up probe with the tip immersed in the reagent and schematically indicating a measurement sensor, a magnetically driven stirrer in the measuring cell and a stirring motor with a stirring magnet outside below the measuring cell.

As shown in FIG. 3 at a location indicated schematically in FIG. 5, there is a reaction and measuring cell 21 with an open top 22 to permit the probe 14 to be lowered into the cell and raised again when the probe carrying arm 16 is in the position indicated by dashed lines in FIG. 5. For the second simultaneous analysis there is a second cell 21' with an open top. The sample cup carrying mechanism, and the probe lowering and lifting mechanism, broadly considered, with the mechanism for transferring the probes horizontally, then separating them horizontally, do not constitute the present invention and need not be fully illustrated or described in detail. Each measurement cell 21 or 21' is provided with a measurement sensor 23 communicating with a cavity 24 adapted to be filled to a liquid level higher than the level of the measurement sensor 23 with a suitable reagent such as an enzyme. Oxidase may be used as the enzyme for oxygen rate, and urease for conductivity rate in the analysis for glucose and blood urea nitrogen, respectively. There is a magnetic stirrer 26 mounted rotatably in the lower portion of the cavity 24 within the body of reagent 25 adapted to be rotated by a magnet 27 carried by a stirring motor 28. Reagent inlet and outlet ports 29 and 30 are also provided. The general arrangement may be similar to that described in the previously identified U.S. Pat. No. 3,701,716.

As shown in FIG. 3, in order to ensure complete drainage of reagent and the previously measured sample after analysis has been completed, the inlet port 29 and the outlet port 30 are preferably located at the terminus of a passageway 32 extending downward from the measuring cell cavity 24 so that the ports 29 and 30 are well below the lowermost portion of the cavity 24. A programmer 33, represented schematically by a rectangle in FIG. 4, is provided to cause the moving mechanism to be energized and the measurement sensor 23 to be activated in the desired sequence. The programmer 33 may be of any suitable type such as mechanical, cam operated, electrical drum switch, electronic with time delay elements or solid state, or a combination thereof. The manner of forming, setting or adjusting suitable solid state programmers to achieve the desired sequence of operations is not specifically described in the present application, but a preferred sequence of operations will be described.

As shown in FIG. 6, there is a sample pump 35, for drawing sample into the probe 14 from the sample cup 14 13 during a suction stroke and ejecting the sample into the reacting and measuring cell 21 during a return stroke. There is also a water reservoir 36, and there is a changeover valve 37, for connecting the pump line 15 either to the probe 14 through tubing 38 (FIG. 6a) or to the water reservoir 36 through tubing 39 (FIG. 6).

OPERATION

The programmer 33 is so designed that when a sample cup 13 reaches the sample pick-up position, the probe 14 draws in a first air bubble 42 by application of suction to the tubing 15 by a suitable mechanism such as the piston or plunger type pump or actuator 35, for example. The probe is then inserted into the sample cup 13, and pump 35 is again actuated to draw a sample slug 43 into the probe. The probe carrying arm 16 is then turned to its upward position to lift the probe from the sample cup. As will be explained more specifically in connection with FIG. 7, the first air bubble serves to separate the sample 43 from a slug 44 or a portion of a column of water. This separation by the first air bubble prevents the sample from diffusing into the water slug.

The probe or probes are transferred horizontally, seaprated horizontally, and then positioned over the open tops 22 and 22' of the two measurement cells 21 and 21'. While the probe is in the position over the measuring and reaction cell 21, the sample pump suction stroke advances again to draw a second air bubble 47 (FIG. 7) into the probe tip 46. This second air bubble in the probe tip prevents diffusion of reagent into the probe after the probe has been lowered into the reacting cell 21 and before the sensor 23 has been activated in order to avoid premature reaction and dissipation of a portion of the sample before the analysis has commenced and thus eliminates such a source of error in the reading produced by the sensor.

Figure 1:
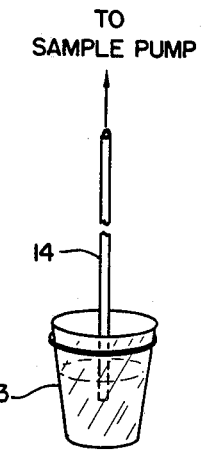
FIG. 1 is a schematic diagram of a portion of the apparatus including one of the sample cups with the probe inserted therein.
Figure 2:
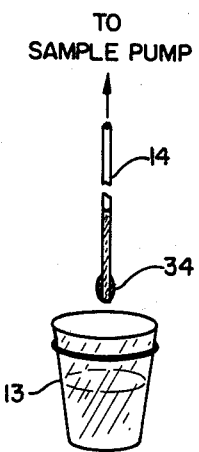
FIG. 2 is a schematic diagram corresponding to FIG. 1 but with the probe lifted from the sample cup and showing external sample residue coating on the probe tip.

A residual amount of sample 34 as illustrated in FIG. 2 will coat the outer surfade of the probe 14. The residual amount will vary with the depth of immersion, the viscosity of the sample, the temperature and the material of the probe. This variance in the outer residual coating would add to the non-repeatability of the total measurement if means were not provided for cleaning the probe before measurement as well as between uses of the probe for picking up different samples.

In procedures previously employed, typically the probe 14 is removed from the measuring cell 21 or 21' as soon as the measured sample amount has been injected into the reacting reagent 25 and varying amounts of sample residue are left behind in the reagent 25 along with the metered amount of sample. This residual amount of sample is included in the measurement being made. An additional amount of residue remains on the probe tip and contaminates subsequent samples as well as rendering readings inaccurate.

In accordance with the invention both types of error contribution in automatic apparatus by the varying residue of sample are overcome. After the probe 14 has been lifted from the cup 13 and transferred to the measuring cell 21, the tip of the probe 14 is purposely left in the reagent 25 in measurement cell 21. The tip 46 of the probe 14 is held in the measuring and reacting cell 21 for a sufficient length of time for sample material coating the probe tip to be consumed by the reagent 25, before the measured amount of sample is injected from the probe 14 and before the electronic signal from the sensor 23 is processed for analytical purposes, for example before the signal is read out. This may be a brief period, e.g. 5–15 seconds, in glucose analysis. This eliminates the effect of indefinite amount of the sample residue added to the metered amount as a source or contributor to the error or uncertainty of the measurement then being made. Such as error would take place without cleaning the probe tip because the measurement depends upon the quantity of sample reacting. Furthermore, the procedure of cleaning the probe tip eliminates a build-up of material, usually protein from serum on a probe tip that often causes additional sample pick-up problems of cleanliness and cross-contamination of samples the probe enters as the probe is inserted into successive sample cups.

The stirrer 26 is preferably in operation during the cleaning process to assure bringing ample reagent into contact with the residue sample on the probe tip.

Owing to the fact that the cell 21 contains an excess of reagent, the residue sample and the reagent reacting therewith disappear when the residue has been consumed. Consequently, the cleaning procedure does not interfere with the measurement made when metered sample has been injected from the probe into the cell 21.

It is an important feature of the invention that the sample probe is left in the reacting cell and reagent to clean it of the variable previous sample that coats the outer surface, before the metered amount of a new sample is delivered, the sensor is activated and the reaction is measured.

It is thus seen that the invention improves precision of measurements particularly in microliter sample sizes. It also reduces or eliminates carryover of sample to the next sample. It makes a more efficient system as a result of the reduction or elimination of extra cleaning apparatus built into many current devices, particularly automatic or semi-automatic analyzers, especially those instruments that analyze biological, human or animal fluids that have a tendency to vary greatly in many of their properties, such as viscosity and tendency to form protein solids and the like. It also eliminates or reduces the frequent need for manual cleaning of the probe tip and the tendency of probe tips to plug up frequently.

An adjustment and setting for the programming apparatus, generally indicated by the reference numeral 33, which may be utilized is illustrated in the following table, referring to only one of the probes and disregarding water and air slug introduction.

SIMPLIFIED PROGRAM

1. Position the first sample cup 13 under the probe 14 in the probe pick-up position.
2. Lower the probe 14.
3. Actuate the sample fill pump to draw sample into the probe.
4. Raise probe 14.
5. Transfer probe 14 horizontally by movement of turntable or arm 18 to position probe 14 over the measurement cell 21.
6. Lower probe 14.
7. Energize stirrer 26 for circulating reagent around the probe 14 and cleaning it.
8. Operate sample pump 35. in the reverse direction to eject sample into the measurement cell 21.
9. Activate measurement sensor 23 and electronic circuitry to record analysis.
10. De-activate measurement sensor 23.
11. Stop stirrer 26.
12. Drain spent reagent and sample from measurement cell 21 by stroke of drain/wash pump (not shown), rinse probe tip of reagent via wash water and drain of wash water.
13. Raise probe 14.
14. Actuate reagent fill pump (not shown) to refill measuring cell 21 with reagent.
15. Return probe 14 to sample pick-up position
16. Position another sample cup 13 under the probe and repeat steps 2–15 for the second sample followed by successive repetition of steps 1–15 with successive samples.

Steps 11, 12 and 13 may be carried out simultaneously followed by steps 14, 15, 16 simultaneously carried out.

For simplicity the basic aspects of the operating procedure have first been described. Advantageously, however, as explained distilled water from a supply container 36 is also injected into the measurement cell when the sample is injected for causing all of the sample to leave the probe 14 and enter the cell 21. For example, 13.7 microliters of sample are injected into the measurement cell, followed by 13.7 microliters of water. This is done by maintaining a water column in and above the probe 14 and utilization of a suitable three-way, or changeover valve 37 connecting the pump line 15 with a line 38 from the sample probe 14 and a line 39 from the water supply 36 to cause water to be pumped into the cylinder of pump 35 by a water pump 40 or drawn in by the sample pump 35 in its suction stroke after it has drawn in the sample.

Water is used to fill the cylinder of the pump 35, the upper end of the probe 14, and connecting tubing 15 and 38, because water is an incompressible liquid and produces uniform intake of sample for a given length of stroke of the sample pump 35. The pump 35 displaces an incompressible liquid instead of a compressible substance such as air. Consequently, each cycle of operation results in a sample of the same volume. This avoids the possibility of lack of uniformity of the sample volume from cycle to cycle which might occur if the pump cylinder, connecting tubing and upper portion of the probe 14 were air filled. Owing to the possibility of variations in atmospheric pressure, temperature, and densities of different samples, the extent of motion of sample into the probe 14 by suction in an air-filled connection between the pump 35 and the sample drawn into the probe tip 46 could vary from test to test for a given pump stroke.

On the other hand, because the pump 35 has a uniform stroke from position to position as shown in FIG. 9, and the liquid displaced by pump action is incompressible the sample volume picked up and ejected is the same for every cycle of operation.

Owing to the fact that water fills the upper end of the probe 14, the lines 15 and 38 and the cylinder of the pump 35, the water slug 44 (FIG.7) is really not a discrete body of water but only a portion of a water column which moves back and forth during opposite strokes of the pump 35, while the changeover valve 37 is in the position to connect the sample pump line 15 to the probe 14 through the line 38. The length of the portion of the water column representing the water slug 44 is determined by the relative lengths of portions of the pump stroke during which sample and air are drawn in the sample with water are being ejected.

The probe 14 has a tip 46 of sufficiently small bore to hold water or liquid sample in the probe by an air seal and prevent overflow by gravity.

As already explained, drawing in a slug or bubble of air 42 to separate the sample 43 in the tubing from the water 44 (FIG. 7) prevents diffusion of sample into the water slug 44 and even higher in the water column, which would cause a portion of the sample to be effectively lost. The reason water is caused to flow into the pump cylinder after the pump 35 has made a suction stroke is to replenish the supply of water in the water column in the tubes 15 and 38 and ultimately the upper end of the probe 14.

In effect, water and sample enter the probe 14 from opposite directions so that drawing in an air bubble before drawing in sample results in separation of sample and water by the air bubble.

The sample pump piston 45 is caused to move a short distance after the probe tip 46 has been lifted out of the sample cup 13 and before it has been lowered into the measurement cell 21, causing the sample pump 35 to introduce a second air bubble 47 in the probe tip 46 in order to prevent diffusion of reagent into the probe tip 46 and thus initiate premature reaction. This is done by moving the piston 45 of the sample pump somewhat further in its upward stroke while the probe tip 46 is in an upper position, not in either sample cup 13 or cell 21, and before the probe is lowered into the measuring cell 21 and before sample mixed with water is ejected to the measuring cell.

Owing to the fact that the quantity of reagent is large in relation to the size of the sample and there is sufficient excess reagent 25 in the measurement cell 21 to consume the residual sample 34 without affecting the analysis by the action of the reagent in the subsequently injected sample, it is not necessary to flush reagent through the cell 21 during the tip cleaning operation. Nevertheless the invention does not exclude actuation of reagent fill and drain pumps to promote cleaning, especially in apparatus where the compositions of sample and reagent are different from those assumed for biological analyses such as blood serum and an enzyme, respectively.

The apparatus including solid state circuitry for effecting the sequential operation of the elements previously referred to is accomplished by the programmer 33 to which reference has already been made. The sequence of operations of the valve 37 in relation to the pump operation and to the operation of certain other elements of the apparatus is indicated in the graph of FIG. 9. In FIG. 9 the curve 48 represents the pump stroke or motion of the piston 45 in relation to an arbitrary scale in which significant points are indicated by various numbers in terms of degrees which are not intended to represent actual angular positions of rotary mechanism driving the pump piston or acting in conjunction therewith. The curve 48 in the upward or positive direction represents the suction stroke of the piston 35 and motion in the downward or negative direction toward the base line represents the sample ejection stroke of the piston 35. The curve 49 of FIG. 9 represents the motion of the water valve 37 with areas above the curve 49 representing times when the valve 37 connects the pump 35 to the probe 14 through the probe line 38 and areas below the line 49 and above the base line 51 of the curve 49 representing the times when the pump 35 and the sample pump line 15 are connected to the water line 39 and disconnected from the probe 14 and the probe line 38.

The sequence of operations, especially with respect to the movement of the sample during the improved procedure, is as follows:- The sample pump 35 picks up an air slug first while the sample pump is moving between the 270° and 290° position of curve 48 of FIG. 9 while the probe tip 46 is in an upper position, that is not either the measurement cell 21 or the sample cup 13, and this may take place while the crane 16–18 is transferring the probe from the measurement position to the sample position. While this is taking place fresh reagent is being delivered to the measurement cell 21 by means not shown as they are not a part of the present invention. The crane having been energized to move the probe 14 to a position over the sample cup 13, it is energized to lower the probe 14, dipping the tip 46 into the sample cup. The upward stroke of the sample pump 35 between the point 310° and 350° on curve 48 of FIG. 9 causes sample to be drawn into the probe 14, for example a sample of 13.7 microliters. The probe 14 then rises and the valve 37, as indicated by curve 49 of FIG. 9, moves to the position for switching the pump line 15 to the water line 39 to replenish the supply of water in the lines 15 and 38 and the upper end of the probe 14.

Owing to the fact that there is already water in the upper end of the probe 14, there is in effect a slug of water 44 above the first air bubble 42 (FIG. 8). The size of the water slug 44 is determined by the physical constants of the apparatus and may also consist of 13.7 microliters. The sample pump 35 may be connected through line 39 and valve 37 to receive water pumped between the 40° and 80° positions of the sample pump as indicated in curve 48 of FIG. 9. The crane 16–18 then moves the probe 14 back over the measuring cell 21. Valve 37 switches to the position which connects pump 35 to the probe 14. The sample pump then moves slightly further during the time period between the 120° and 140° positions of the pump, as indicated in curve 48 of FIG. 9 to pick up the air slug 47 in the tip 46 of the probe 14. During the time period represented by a distance between 120° and 140° positions of curve 48 of FIG. 9 the probe 14 is descending into the measuring cell 21. However, a time delay occurs while the probe is in the measuring cell and the stirrer is still running to expose the sample residue coating 34 on the outside of the probe 14 thoroughly to reagent and enable it to be consumed before the fresh sample is ejected into the measurement cup and the measurement is made. Then the piston 45 of the sample pump 35 executes its return stroke as represented by the position of the curve 48 of FIG. 9 between the 140° and 200° points to eject the separate slugs of sample and water into the measuring cell 21, the stirrer 26 having started rotating at the 140° point of the curve 48. The water slug 44 following the sample 43 washes all the sample out of the probe into the reaction cell 21. It will be understood that the curve 48 represents motion of the pump piston 45 in relation to its operating mechanism, such as a cam, and the spacing between points on the curve 48 is unrelated to actual time periods in the sequence of operations of the entire system with which the present invention is employed. The bar graph portion 52 of FIG. 9 represents the timing of related operations controlled by the programmer 53 in relation to points in the pump stroke represented by the curve 48.

Any suitable means may be provided for producing the sample pump stroke represented by the curve 48 of FIG. 9. For example, if camming mechanism is employed it may take the form illustrated in FIG. 10 of the grooved disc cam 53 having a groove 54 in one face thereof cooperating with a cam follower 55 connected to the pump piston 45 by suitable linkage 56. In FIG. 10 the lift in the portion 57 between the 270° and 290° points on the cam provides the means for drawing air into the probe tip 46 before sample is drawn in and the lift in the portion 58 of the cam groove between the 120° and 125° points provides the lift for drawing the second air bubble into the probe tip 46 before sample is ejected into the measurement cell. The angular positions marked in FIG. 10 correspond to those in the curve 48 of FIG. 9. The valve motion represented by the curve 49 of FIG. 9 may also be produced by a cam groove (not shown) on the opposite face of the cam disc 53. The cycling of the rotation of the cam disc 53 is also controlled by the programmer 33.

Although we have herein shown and described our invention in what we have construed to be the most practical and preferred embodiment, it is recognized that departures may be made therefrom, within the scope of our invention, which is not limited to the details disclosed herein, but is to be accorded the full scope of the claims so as to embrace any and all equivalent structures, methods and devices.

What is claimed is:

1. An improved method of picking up and dispensing a quantity of liquid sample material for analysis using a sample pick-up probe comprising the steps of:
   inserting the probe into the sample material and drawing a quantity of the sample into the probe;
   removing the probe from the sample material and drawing a bubble of air into a tip end of the probe;
   inserting the probe into a reagent chemically reactive with the sample material for a period of time sufficient for the reagent to consume any residue of sample material adherent to the outside of the probe, the air bubble isolating the sample in the probe from the reagent; and
   subsequently ejecting the air bubble and at least a portion of the sample material from the probe for analysis.

2. An improved method for picking up and dispensing a quantity of liquid sample material for analysis using a sample pick-up probe comprising the steps of:
   inserting the probe into the sample material and drawing a quantity of the sample into the probe;
   removing the probe from the sample material and drawing a bubble of air into a tip end of the probe;
   inserting the probe into a reagent chemically reactive with the sample material for a period of time sufficient for the reagent to consume any residue of sample material adherent to the outside of the probe, the air bubble isolating the sample in the probe from the reagent, and then, with the probe in the reagent, ejecting the air bubble and at least a portion of the quantity of sample material from the probe for reaction therewith.

3. The method of claim 2 wherein sensor means is provided for monitoring the reaction to derive a signal providing a measurement of the concentration of a constituent of the sample material, and wherein the method further includes the step of inhibiting said measurement during the period of time that the probe is inserted in the reagent prior to the ejection of sample material from the probe.

4. In a liquid sample analyzer of the type having an analysis chamber adapted to receive a sample material and a reagent chemically reactive therewith, sensor means for monitoring the sample-reagent reaction to derive a signal providing a measurement of the concentration of a constituent of the sample material, means for presenting a plurality of samples for analysis, a sample pick-up probe, probe control means including means for inserting the probe into a sample and drawing a quantity of sample material into the probe, means for transferring the probe to a postion adjacent the analysis chamber, means for inserting the probe into the reagent in the analysis chamber, means for ejecting the sample material from the probe for analysis upon reaction with the reagent, and means for repeating the above-described sequence for each succeeding sample to be analyzed, the improvement comprising:
   means for drawing a bubble of air into a tip end of the probe after drawing the quantity of sample material into the probe and before inserting the probe into the reagent;
   means for maintaining the probe in the reagent for a period of time sufficient for the reagent to consume any residue of sample material adherent to the outside of the probe, the air bubble isolating the sample in the probe from the reagent; and
   means for subsequently ejecting the air bubble and at least a portion of the sample material from the probe into the analysis chamber and the reagent therein for analysis.

5. The analyzer of claim 4 further including means for inhibiting said measurement during the period of time that the probe is inserted in the reagent prior to the ejection of sample material from the probe.

6. Apparatus for picking up and dispensing a quantity of liquid sample material for analysis comprising:
   a sample pick-up probe;
   means for inserting the probe into the sample material and drawing a quantity of the sample into the probe;
   means for removing the probe from the sample material and drawing a bubble of air into the tip end of the probe;
   means for inserting the probe into a reagent chemically reactive with the sample material for a period of time sufficient for the reagent to consume any residue of sample material adherent to the outside of the probe, the air bubble isolating the sample in the probe from the reagent, and then, with the probe in the reagent, for ejecting the air bubble and at least a portion of the quantity of sample material from the probe for reaction therewith.

7. The apparatus of claim 6 further including sensor means for monitoring the reaction to derive a signal providing a measurement of the concentration of a constituent of the sample material; and means for inhibiting said measurement during the period of time that the probe is inserted in the reagent prior to the ejection of sample material from the probe.

* * * * *